United States Patent
Morancy-Meister et al.

(10) Patent No.: US 8,252,029 B2
(45) Date of Patent: Aug. 28, 2012

(54) EXPANDABLE INTERSPINOUS PROCESS SPACER WITH LATERAL SUPPORT AND METHOD FOR IMPLANTATION

(75) Inventors: Anne Catherine Morancy-Meister, Dachsen (CH); Thomas Egli, Volketswil (CH); Rosemary Thompson, Seen (CH); Nicole Gronau, Zurich (CH); Walter Gross, Ossingen (CH); Michael Motzko, Gröbenzell (DE); Fabio Bernhardsgrütter, Winterthur (CH); Jochen Reinmuth, Winterthur (CH)

(73) Assignee: Zimmer GmbH, Winterthur (CH)

( * ) Notice: Subject to any disclaimer, the term of this patent is extended or adjusted under 35 U.S.C. 154(b) by 1055 days.

(21) Appl. No.: 12/035,165

(22) Filed: Feb. 21, 2008

(65) Prior Publication Data
US 2009/0216274 A1   Aug. 27, 2009

(51) Int. Cl.
*A61B 17/70* (2006.01)
(52) U.S. Cl. ....................................................... 606/249
(58) Field of Classification Search .......... 606/246–249, 606/86 A, 86 R, 279, 99; 623/17.11–17.16
See application file for complete search history.

(56) References Cited

U.S. PATENT DOCUMENTS

| | | |
|---|---|---|
| 5,011,484 A | 4/1991 | Breard |
| 5,092,866 A | 3/1992 | Breard et al. |
| 5,496,318 A | 3/1996 | Howland et al. |
| 5,645,599 A | 7/1997 | Samani |
| 5,836,948 A | 11/1998 | Zucherman et al. |
| 5,888,220 A | 3/1999 | Felt et al. |
| 5,989,256 A | 11/1999 | Kuslich et al. |
| 6,074,390 A | 6/2000 | Zucherman et al. |
| 6,187,048 B1 | 2/2001 | Milner et al. |
| 6,238,397 B1 | 5/2001 | Zucherman et al. |
| 6,364,883 B1 | 4/2002 | Santilli |
| 6,419,677 B2 | 7/2002 | Zucherman et al. |
| 6,582,433 B2 | 6/2003 | Yun |
| 6,652,527 B2 | 11/2003 | Zucherman et al. |
| 6,652,587 B2 | 11/2003 | Felt et al. |
| 6,733,534 B2 | 5/2004 | Sherman |
| 6,946,000 B2 | 9/2005 | Senegas et al. |
| 7,001,431 B2 | 2/2006 | Bao et al. |
| 7,048,736 B2 | 5/2006 | Robinson et al. |
| 7,087,083 B2 | 8/2006 | Pasquet et al. |
| 7,101,375 B2 | 9/2006 | Zucherman et al. |
| 7,846,185 B2 * | 12/2010 | Carls et al. ................... 606/249 |
| 2002/0095154 A1 | 7/2002 | Atkinson et al. |
| 2004/0092653 A1 | 5/2004 | Ruberti et al. |
| 2004/0181282 A1 | 9/2004 | Zucherman et al. |

(Continued)

FOREIGN PATENT DOCUMENTS
WO   2006089085 A2   8/2006
(Continued)

*Primary Examiner* — Eduardo C Robert
*Assistant Examiner* — Steven Cotroneo
(74) *Attorney, Agent, or Firm* — Seager Tufte & Wickhem LLC

(57) ABSTRACT

An interspinous process spacer and method of implanting same is provided for maintaining separation between adjacent spinous processes of adjacent vertebrae. The spacer has two lateral portions and a medial portion therebetween, the medial portion adapted to reside between the adjacent superior and inferior spinous processes in the deployed configuration and the lateral portions each comprise a superior lateral portion and an inferior lateral portion adapted to reside on the lateral side of the respective superior and inferior spinous process in the deployed configuration to maintain positioning of the interspinous process spacer between the two adjacent vertebrae. The lateral portions each comprise an expandable lateral member.

24 Claims, 11 Drawing Sheets

U.S. PATENT DOCUMENTS

| | | |
|---|---|---|
| 2004/0249379 A1 | 12/2004 | Winslow et al. |
| 2005/0102028 A1 | 5/2005 | Arnin et al. |
| 2005/0203512 A1 | 9/2005 | Hawkins et al. |
| 2005/0245929 A1 | 11/2005 | Winslow et al. |
| 2005/0261768 A1 | 11/2005 | Trieu |
| 2006/0004447 A1 | 1/2006 | Mastrorio et al. |
| 2006/0064165 A1 | 3/2006 | Zucherman et al. |
| 2006/0085070 A1* | 4/2006 | Kim .......................... 623/17.11 |
| 2006/0089654 A1 | 4/2006 | Lins et al. |
| 2006/0122620 A1 | 6/2006 | Kim |
| 2006/0235386 A1 | 10/2006 | Anderson |
| 2006/0241601 A1 | 10/2006 | Trautwein et al. |
| 2006/0241610 A1 | 10/2006 | Lim et al. |
| 2006/0241613 A1 | 10/2006 | Bruneau et al. |
| 2006/0241614 A1 | 10/2006 | Bruneau et al. |
| 2006/0265066 A1 | 11/2006 | Zucherman et al. |
| 2006/0271055 A1 | 11/2006 | Thramann |
| 2006/0271194 A1 | 11/2006 | Zucherman et al. |
| 2006/0293662 A1 | 12/2006 | Boyer, II et al. |
| 2007/0005064 A1 | 1/2007 | Anderson et al. |
| 2007/0016303 A1 | 1/2007 | Jackson |
| 2007/0073292 A1* | 3/2007 | Kohm et al. .................... 606/61 |
| 2007/0250060 A1 | 10/2007 | Anderson et al. |
| 2007/0282340 A1* | 12/2007 | Malandain ...................... 606/69 |
| 2008/0027438 A1* | 1/2008 | Abdou ........................... 606/61 |
| 2009/0326581 A1* | 12/2009 | Galley et al. .................. 606/249 |

FOREIGN PATENT DOCUMENTS

| | | |
|---|---|---|
| WO | 2006116853 A1 | 11/2006 |

* cited by examiner

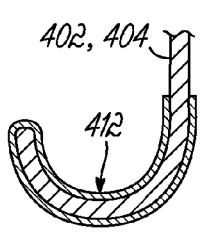
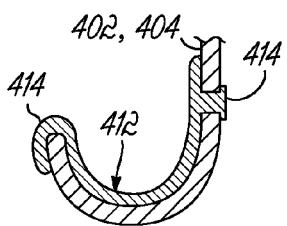
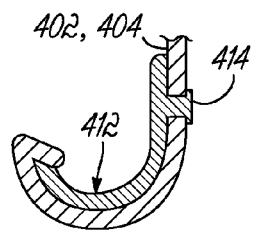
FIG. 42    FIG. 43    FIG. 44
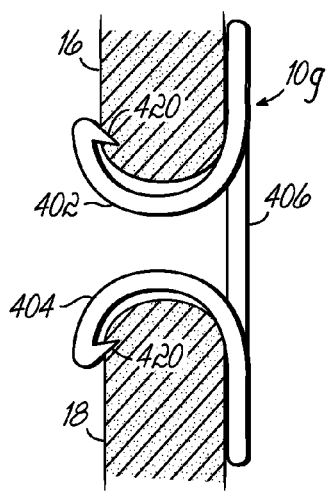
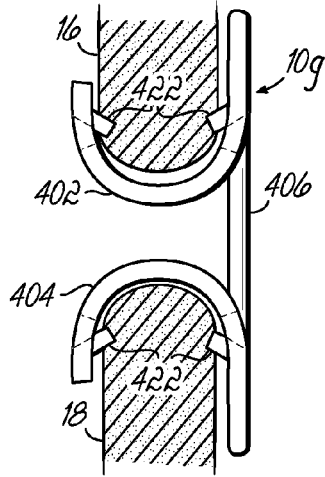
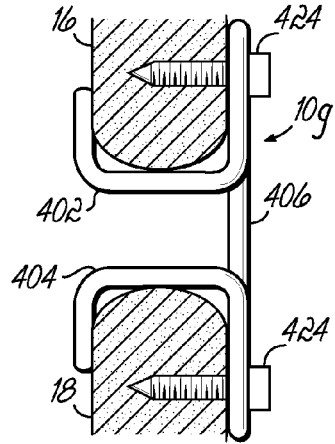
FIG. 45    FIG. 46    FIG. 47
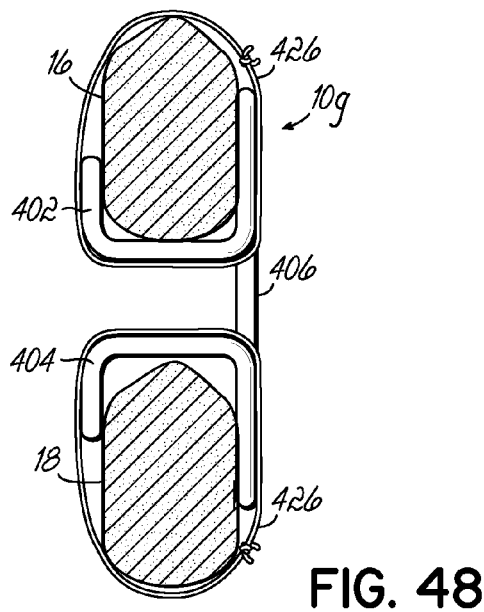
FIG. 48

EXPANDABLE INTERSPINOUS PROCESS SPACER WITH LATERAL SUPPORT AND METHOD FOR IMPLANTATION

FIELD OF THE INVENTION

The present invention relates generally to devices for treating spinal stenosis, and more particularly to interspinous process spacers that can be implanted in a minimally invasive manner to treat spinal stenosis.

BACKGROUND OF THE INVENTION

A large majority of the population will experience back pain at some point in their lives that results from a spinal condition. The pain may range from general discomfort to disabling pain that immobilizes the individual. One type of adverse spinal condition is spinal stenosis, which occurs when the spinal canal or nerve root canals become too narrow and reduce the space for the passage of blood vessels and nerves.

Lumbar spinal stenosis ("LSS", and sometimes called sciatica) is a condition of the spine characterized by a narrowing of the lumbar spinal canal. With lumbar spinal stenosis, the spinal canal narrows and pinches the spinal cord and nerves, causing pain in the back and legs. It is estimated that approximately 5 in 10,000 people develop LSS each year. For patients who seek the aid of a physician specialist for back pain, approximately 12-15% are diagnosed as having LSS.

Several causes of spinal stenosis have been identified, including aging, heredity, arthritis, and changes in blood flow to the lower spine. Aging is believed to be the most common cause, because as a person ages the ligaments connecting the bones of the spine can thicken and spurs may develop on the bones and into the spinal canal. The cushioning discs between the vertebrae also frequently deteriorate, and the facet joints may begin to break down. Over time, loss of disk height in the lumbar regions can result in a degenerative cascade with deterioration of all components of a motion segment resulting in segment instability and ultimately in spinal stenosis. During the process of deterioration, disks can become herniated and/or become internally torn and chronically painful. When symptoms seem to emanate from both anterior (disk) and posterior (facets and foramen) structures, patients cannot tolerate positions of extension or flexion. Heredity is believed to play a role in some cases because it may cause some people to have a smaller than average spinal canal, typically leading to LSS symptoms even at a relatively young age.

The most common symptoms of spinal stenosis are pain and difficulty when walking, although numbness, tingling, hot or cold feelings in the legs, and weakness or tiredness may also be experienced. In extreme cases, spinal stenosis can cause cauda equina syndrome, a syndrome characterized by neuromuscular dysfunction that may result in permanent nerve damage.

Common treatments for LSS include physical therapy (including changes in posture), medication, and occasionally surgery. Changes in posture and physical therapy may be effective in flexing the spine to enlarge the space available to the spinal cord and nerves—thus relieving pressure on pinched nerves. Medications such as NSAIDS and other anti-inflammatory medications are often used to alleviate pain, although they are not typically effective at addressing the cause of the pain. Surgical treatments are more aggressive than medication or physical therapy, but in appropriate cases surgery may be the best way to achieve a lessening of the symptoms associated with LSS.

The most common surgery for treating LSS is decompressive laminectomy, in which the lamina of one or more vertebrae is removed to create more space for the nerves. The intervertebral disc may also be removed, and the vertebrae may be fused to strengthen unstable segments. The success rate of decompressive laminectomy has been reported to be in excess of 65%, with a significant reduction in LSS symptoms being achieved in many cases.

More recently, a second surgical technique has been developed in which the vertebrae are distracted and an interspinous process spacer is implanted to maintain the desired separation between the segments. This technique is somewhat less invasive than decompressive laminectomy, which may provide significant benefits to patients experiencing LSS symptoms.

As with other surgeries, when performing surgery to implant an interspinous process spacer, one consideration is the size of the incision that is required to allow introduction of the device. Medical treatments that can be performed in a less invasive manner are greatly sought after by the medical community and patients alike. In some procedures, less invasive techniques are advantageous because they have shorter recovery periods, result in little to no blood loss, and greatly decrease the chances of significant complications. Moreover, less invasive techniques are generally less expensive for the patient.

In view of the many advantages of less invasive procedures, it would be highly advantageous to have an interspinous process spacer and an associated procedure amenable to less invasive techniques. The present invention addresses that need.

SUMMARY OF THE INVENTION

The present invention addresses these and other problems associated with the prior art by providing a customized interspinous process spacer and associated method to insert it into a medical patient. The interspinous process spacer is to act as a spacing device for the spinous processes of two adjacent vertebrae. The interspinous process spacer is used to distract the vertebrae and relieve pressure on the posterior wall of the intervertebral disc. Furthermore, the interspinous process spacer is expected to relieve pain associated with the spinal canal and/or neural foramen stenosis, as well as potentially relieving pain associated with degenerative facet joints. The interspinous process spacer of the present invention will allow controlled flexion and limited extension at the implanted level.

According to one embodiment of the present invention, an interspinous process spacer is provided for maintaining separation between adjacent superior and inferior spinous processes of two adjacent vertebrae when in a deployed configuration, which comprises a first lateral portion, a second lateral portion, and a medial portion therebetween, wherein the medial portion is adapted to reside between the adjacent superior and inferior spinous processes in the deployed configuration to maintain separation therebetween. The first and second lateral portions each comprise a superior lateral portion adapted to reside on the lateral side of the superior spinous process in the deployed configuration and an inferior lateral portion adapted to reside on the lateral side of the inferior spinous process in the deployed configuration to maintain positioning of the interspinous process spacer between the two adjacent vertebrae. The first and second lateral portions each comprise an expandable lateral member that is expandable from an insertion configuration to the deployed configuration, and at least one of the first and second lateral portions comprises a lateral support member within the expandable lateral member, the lateral support member configured to be deformable for the insertion configuration and expanded in the deployed configuration. The expandable member may be expanded with a flowable material, such as a polymer, for filling the expandable member to the geometry.

In some embodiments of the invention, the medial portion may include a rigid medial member positioned between the superior and inferior spinous processes to maintain separation therebetween. The rigid member may be tubular in shape. In this instance, the medial portion may further comprise an expandable medial member, either positioned within the hollow portion of the tubular rigid medial member, or positioned surrounding the tubular rigid medial member. Alternatively, the expandable lateral portions may be connected to the rigid medial member with no expandable medial member. In any of these embodiments, the opposing lateral portions reside outside the rigid medial member and assist in maintaining the position of the interspinous process spacer. In yet another alternative embodiment, the opposing lateral portions and the medial portion are formed by expandable members, with no rigid medial member.

Another aspect of the invention is a method for implanting the interspinous process spacer for maintaining separation between adjacent superior and inferior spinous processes of two adjacent vertebrae. In one embodiment of the invention, the method comprises introducing a tubular delivery device to a region between the adjacent superior and inferior spinous processes and introducing an interspinous process spacer through the tubular delivery device in a non-expanded, insertion configuration to the region. The interspinous process spacer comprises an expandable member having a distal lateral portion with a distal lateral support member therein, a medial portion, and a proximal lateral portion with a proximal lateral support member therein. The method further includes positioning the interspinous process spacer in the region with the distal lateral portion on a distal side of the spinous processes, the medial portion between the spinous processes, and the proximal lateral portion on a proximal side of the spinous processes, and then retracting the tubular delivery device and expanding the expandable member and the distal and proximal lateral support members to an expanded, deployed configuration.

BRIEF DESCRIPTION OF THE DRAWINGS

A more complete appreciation of the invention and many of the attendant advantages thereof will become readily apparent with reference to the accompanying drawings. These drawings, which are incorporated in and constitute part of this specification, illustrate embodiments of the invention and, together with a general description of the invention given above, and the detailed description given below, serve to explain the principles of the invention.

FIG. 42 through FIG. 44 show in schematic cross-sectional view additional detail of embodiments of the end supports of FIG. 32.

FIG. 45 through FIG. 48 illustrate in rear elevational view alternative fixation methods for the interspinous process spacer of FIG. 32.

DETAILED DESCRIPTION

Figure 1:
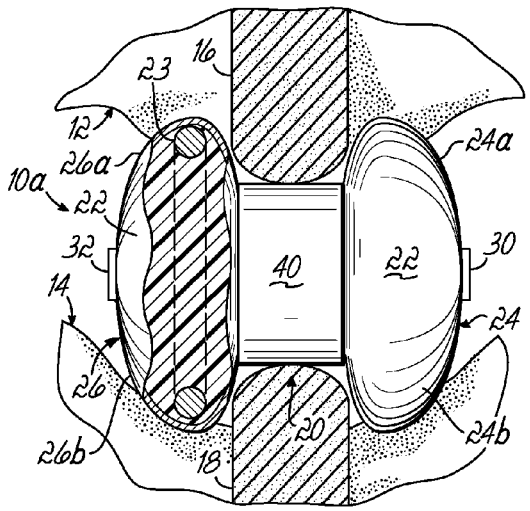
FIG. 1 is a rear elevational view of an interspinous process spacer in the form of an H-shape according to one aspect of the present invention, wherein two expandable lateral members are attached to a rigid medial member.
Figure 2:
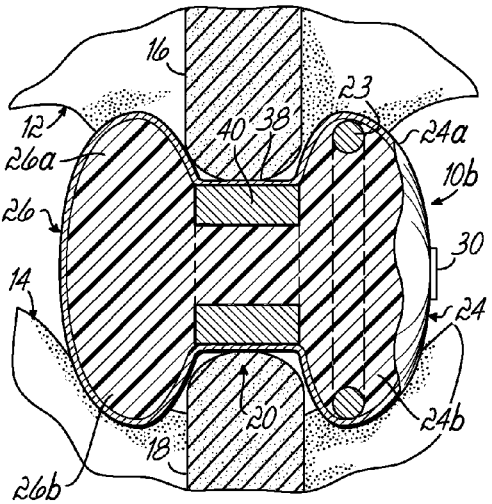
FIG. 2 is a rear elevational view of an interspinous process spacer in the form of an H-shape according to one aspect of the present invention, wherein the rigid medial member is contained within a medial portion of an expandable member.
Figure 3:
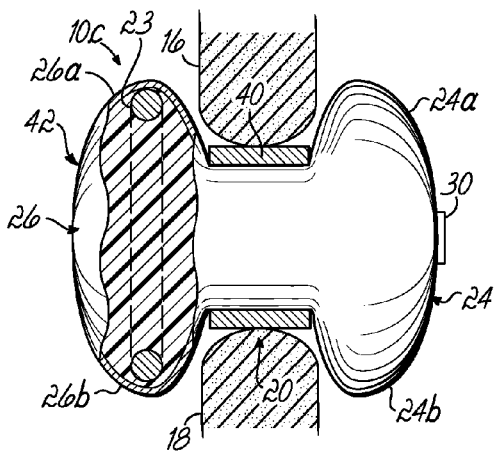
FIG. 3 is a rear elevational view of an interspinous process spacer in the form of an H-shape according to one aspect of the present invention, wherein the rigid medial member surrounds the medial portion of the expandable member.

With reference to the Figures, wherein like numbers denote like parts throughout the several views, exemplary interspinous process spacers 10a-d are shown in accordance with the invention for maintaining a desired spacing between the spinous processes of adjacent vertebrae 12 and 14. According to embodiments of the invention, FIGS. 1-4 illustrate interspinous process spacers 10a-10d that possesses a geometry generally in the form of an H-shape or dumbbell (used interchangeably herein). The spacers 10a-10d comprise a medial portion 20 adapted to reside between adjacent superior spinous process 16 and the inferior spinous process 18. The medial portion 20 may comprise an expandable medial member 38 (FIGS. 2-4) and/or a rigid medial member 40 (FIGS. 1-3).

Spacers 10a-10d further comprise opposing lateral portions 24 and 26, which are located at the lateral ends of the medial portion 20. Each lateral portion 24, 26 consists of a superior lateral portion 24a, 26a adapted to reside on the lateral side of the superior spinous process 16 and an inferior lateral portion 24b, 26b adapted to reside on the lateral side of the inferior spinous process 18, to maintain position of the interspinous process spacer 10a within the desired space when in the expanded, deployed configuration, as shown in each of FIGS. 1-4. Each lateral portion 24, 26 may comprise at least one filling member 30, 32, such as a valve, to allow separate introduction of a flowable material (not shown), if desired, to each lateral portion 24, 26, such as if the medial portion 20 does not sufficiently permit the flow of fluid from one lateral portion to the other and/or where the medial portion 20 includes a rigid medial member 40 that is a solid rod configuration rather than a tubular configuration having a central conduit.

The lateral portions 24, 26 each comprise an expandable lateral member 22 that is expandable from an insertion configuration, shown in FIG. 5C discussed further below, to an expanded, deployed configuration shown in FIGS. 1-4 and 5D-5E. To that end, expandable lateral members 22 may be made of non-compliant material that will assume the desired geometry and position when expanded. In another embodiment, the expandable lateral members 22 may be made of compliant material that will maintain the desired geometry when expanded. Expandable as used herein includes any increase in the volume, dimension, circumference, etc. of a member. Expansion may include a stretching of the material of the member from its natural state whereby the dimensions of the member increases beyond a natural state, like a balloon. Alternatively, expansion may include no stretching of the material, but rather, an unfolding of the material from a collapsed position to its full natural geometry and dimensions. In yet another embodiment, the geometry may be further maintained by casting the expandable lateral member 22 with a fiber reinforcing mesh made to the desired geometry. The expandable lateral members 22 may comprise biocompatible materials, such as polyethylene terephthalate or polyethylene. Other suitable materials may comprise polyacrylates, polypropylene, polyolefin copolymers, polycarbonates, polyesters, ether-ketone copolymers, polytetrafluoroethylene fibers or silk. Of course, other suitable biocompatible materials are possible as well without departing from the scope of the present invention.

One or both of the lateral portions 24, 26 further comprise a lateral support member 23 that resides within the expandable lateral member 22 to support the lateral portions 24, 26 during expansion. The lateral support member 23 is configured to be deformable for the insertion configuration, shown in FIGS. 5C-5D, and expanded or returned to the deployed configuration, shown in FIGS. 1-4 and 5D-5E, after insertion.

In one embodiment, the lateral support member 23 is elastically deformable. In elastic deformation, the amount of deformation is proportional to the amount of applied force or stress. Upon application of stress (e.g., a compressive force), the material of the lateral support member 23 deforms to a configuration suitable for insertion. That stress is maintained either by continually applying the force or by treating the material to temporarily cause it to remain in the stress-state. After insertion, when the stress is removed, either by removing the applied force or by introducing a thermal change that releases the stress, the material completely or substantially resumes its original or undeformed state, i.e., it expands back to the expanded, deployed configuration. A perfectly elastic body will completely resume its shape with no plastic (i.e., permanent) deformation. A minor amount of plastic deformation, however, can be permitted. Shape memory alloys, such as nitinol (a NiTi alloy), can be treated (programmed) to maintain the induced stress, and thus the insertion configuration, until a temperature is applied (e.g., body temperature, a heated or cooled flowable material, a heated or cooled rinse fluid, etc.) that releases the stress, upon which the shape memory alloy remembers and reverts to it's original shape, which is the shape for the desired expanded, deployed configuration.

Thus, the lateral support members 23 may be manufactured to have the desired deployed configuration as the original or natural shape of the material, and the insertion configuration is a deformed state in which the size of the member is altered and/or reduced to allow for minimally invasive insertion into the surgical site between and/or laterally of the adjacent vertebrae 12, 14. After insertion, the deformation is released, allowing the lateral support member 23 to re-assume (expand to) the expanded, deployed configuration.

In one embodiment, the lateral support members are made of a shape memory material programmed to maintain the deformation within a temperature range that encompasses expected room temperature variations, and to release the deformation upon exposure to an elevated temperature. The elevated temperature may correspond to expected body temperatures in the applicable vertebral region, such that the lateral support members are self-expanding in the applicable vertebral region upon reaching temperature equilibrium with the body temperature. Alternatively, or in addition, a heated fluid may be used to bring the lateral support members up to the elevated temperature, such as by heating the flowable material. In another embodiment, the shape memory material may be programmed to release the deformation upon exposure to a low temperature (e.g., below expected room temperatures), which may be achieved by cooling a fluid.

In yet another embodiment, the lateral support members are made of a spring-type material that may be deformed to a contracted or collapsed state by a delivery tube for insertion to the vertebral region. Upon removal of the delivery tube, the material springs back to its full shape. Thus, the spring-type material is self-expanding in the vertebral region upon removal of the constraining delivery tube.

In FIGS. 1-4, the opposing lateral portions 24, 26 are shown in the expanded, deployed configuration. The means utilized to expand the opposing lateral portions 24, 26 may include a flowable material. In one embodiment, the flowable material may consist of bone cement, polyurethane, silicone, copolymers of silicone and polyurethane, polyolefins, neoprene, nitrile or combinations thereof. Of course, other suitable fluids are possible as a means of expansion without departing from the scope of the present invention.

Another aspect of the invention is the interspinous process spacer 10a-10d may be fixed in the interprocess space by connecting members (not shown) integrated with the medial portion 20 or the lateral portions 24, 26. Exemplary connecting members may include connecting members to allow attachment to the superior and inferior spinous processes 16, 18 by bone darts, fibers of sufficient length to enable tying to the superior and inferior processes 16, 18, or sutures that anchor the interspinous process spacer 10a-10d to neighboring biological tissue, i.e. sutured to adjacent soft tissue such as the interspinous and supraspinous ligament. Moreover, the interspinous process spacer may be designed with tissue ingrowth capability for long-term fixation, if desired. It will be appreciated that manners of fixation known in the art, other than the exemplary manners described herein, may be used without departing from the scope of the present invention.

In the embodiments of FIGS. 1-3, the interspinous process spacers 10a-10c include a rigid medial member 40 in the medial portion 20. The rigid medial member 40 may be comprised of a biocompatible metal or polymer, such as titanium or polycarbonate urethane. Other suitable materials may include poly(lactic acid), poly(glycolic acid), p-dioxanone fibers, polyarylethyl, polymethylmethacrylate, polyurethane, amino acid-derived polycarbonate, polycaprolactone, aliphatic polyesters, calcium phosphate, unsaturated linear polyesters, vinyl pyrrolidone, polypropylene fumarate diacrylate, or mixtures thereof. Of course, other suitable biocompatible materials are possible as well without departing from the scope of the present invention. Additionally, the height of the medial portion 20 may vary between 5 mm and 20 mm.

The interspinous process spacer may have a relationship between the rigid medial member 40 and the expandable members 22, 38 that exists in three general forms. First, in the embodiment depicted in FIG. 1, the rigid medial member 40 may be the medial portion 20 of the interspinous process spacer 10a, with a pair of expandable lateral members 22 forming opposing lateral portions 24 and 26 at the lateral ends of the medial portion 20. In this embodiment, the rigid medial member 40 may be attached to the expandable lateral members 22. In this instance, the expandable lateral members 22 form the opposing lateral portions of the interspinous process spacer after expansion with a flowable material or other fluid and complete the dumbbell or H-shape of the interspinous process spacer 10a. Where the rigid medial member 40 is a solid rod, or the connection between the rigid medial member 40 and the expandable lateral members 22 is such that there is no fluidic coupling between the pair of expandable lateral members 22, then each lateral member may be expanded by introducing fluid through a respective filling member 30, 32. Where the rigid medial member 40 is a cylinder or tube and a fluidic coupling is maintained between the pair of expandable lateral members 22, then a single filling member 30 may be used, or opposed filling members 30, 32 may be used, as desired. Alternatively, no filling members may be provided where a syringe needle can be used to achieve filling of the expandable lateral members 22. In addition, a lateral support member 23 is shown in the lateral portion 26. A second lateral support member 23 may or may not be present in the lateral portion 24. Lateral support member 23, upon expansion, may also cause at least partial expansion of the expandable lateral member 22.

Interspinous process spacer 10b in FIG. 2 illustrates a second relationship where the medial portion 20 comprises a rigid medial member 40 residing within an expandable medial member 38, wherein the rigid medial member 40 is generally shaped in the form of a cylinder or tube. The expandable medial member 38 and the expandable lateral members 22 may together form a single, seamless (one-piece) expandable member 42 that has the deployed configuration generally in the form of the H-shape or dumbbell. Alternatively, the two expandable lateral members 22 and the expandable medial member 38 may be joined to form a single expandable member 42 having seams between the three joined pieces. The expandable medial member 38 and the single, seamless expandable member 42 may be made of the same materials as described above for the expandable lateral members 22. The material of the expandable medial member 38 may be the same or different than the material of the expandable lateral members 22. A single filling member 30 is illustrated in lateral portion 24, contemplating filling through the rigid medial member 40 to the lateral portion 26. It may be appreciated that filling members may be provided in both lateral portions 24, 26, such as depicted in the embodiment of FIG. 1, or no filling members may be provided where a syringe needle can be used to achieve filling of the expandable member 42. In addition, a lateral support member 23 is shown in the lateral portion 24. No lateral support member 23 is present in the lateral portion 26. Lateral support member 23, upon expansion, may also cause at least partial expansion of the expandable lateral member 22.

Interspinous process spacer 10c, illustrated in FIG. 3, represents a complementary third relationship wherein the medial portion 20 comprises the rigid medial member 40, again generally shaped in the form of a tube, but this time surrounding the expandable medial member 38. In this embodiment, the expandable medial member 38 and the expandable lateral members 22 again together form the single expandable member 42 (seamless or with seams) that has the deployed configuration generally in the form of the H-shape or dumbbell. One of the expandable lateral members 22 may be inserted through the rigid medial member 40 to position the expandable medial member 38 within the rigid medial member 40. Again, a single filling member 30 is illustrated in lateral portion 24, contemplating filling through the expandable medial member 38 to the lateral portion 26. As stated above, however, two filling members 30, 32 or no filling member may be used to achieve expansion of the expandable member 42. In addition, a lateral support member 23 is shown in the lateral portion 26. A second lateral support member 23 may or may not be present in the lateral portion 24. Lateral support member 23, upon expansion, may also cause at least partial expansion of the expandable lateral member 22.

Figure 4:
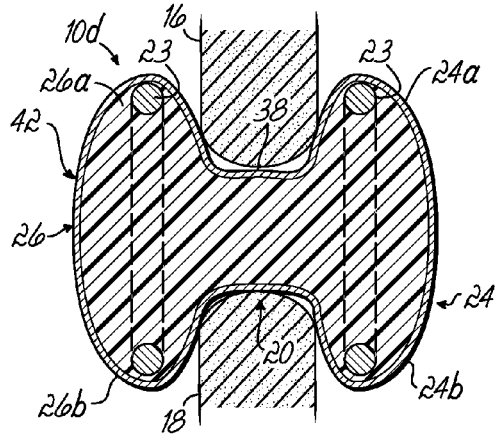
FIG. 4 is a rear elevational view of an interspinous process spacer in the form of an H-shape according to one aspect of the present invention, wherein lateral support members reside in the lateral portions of the expandable member, with no rigid medial member.

In the embodiment illustrated in FIG. 4, interspinous process spacer 10d includes a medial portion 20 having an expandable medial member 38, but no rigid medial member. The expandable medial member 38 and the expandable lateral members 22 again together form the single expandable member 42. In this exemplary embodiment, two lateral support members 23 are contained within the expandable member 42, one in each expandable lateral member 22, to support each of the lateral portions 24, 26 during expansion and in deployment. Lateral support member 23, upon expansion, may also cause at least partial expansion of the expandable lateral member 22. No filling member is depicted, contemplating filling by use of a syringe having a needle (not shown).

The lateral support members 23 may be generally in the form of a circle, ellipse, or a C-shape (see FIGS. 4A and 4B), and constructed of polycarbonate urethane (PCU), nitinol (NiTi) or steel, for example. Moreover, lateral support members 23 may be positioned in the lateral portions 24, 26 and connected by a medial support member 21 across the medial portion 20, as illustrated in FIG. 4C. Advantageously, PCU or nitinol are amenable to elastically deforming or altering the shape of the lateral support members 23 to facilitate delivery of the interspinous process spacer 10a-10d through a tube to the space between the superior and inferior spinous processes 16, 18. After the interspinous process spacer 10a-10d is positioned in the desired space, the lateral support members 23 are allowed to relax to their pre-altered shape. Other shape memory materials besides any specifically mentioned herein may be contemplated for the lateral support members 23.

Figure 5B:
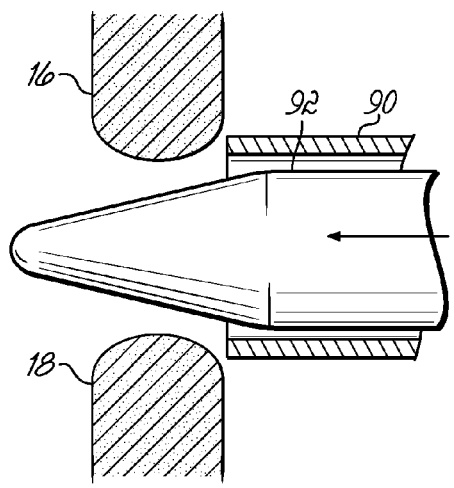
FIGS. 5A-5E illustrate in top and rear elevational views a method of delivering, positioning, and expanding the interspinous process spacer to and in the interprocess space.
Figure 5C:
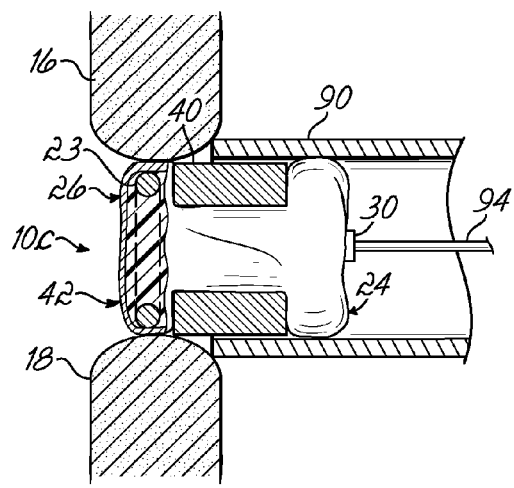

Another aspect of the invention is a method for implanting the interspinous process spacer 10a-d for maintaining separation between adjacent superior and inferior spinous processes 16, 18 of two adjacent vertebrae 12, 14. One exemplary method of implantation is depicted schematically in FIGS. 5A-5E using the interspinous process spacer 10c. The method comprises the exploration of the interspinous region with a delivery tube device 90, as illustrated in FIG. 5A, and opening the interspinous ligament, as shown schematically in FIG. 5B. A dilator 92 may be used to determine the desired diameter of the medial portion of the interspinous process spacer 10c. As illustrated in FIG. 5C, the interspinous process spacer 10c, comprising the rigid medial member 40, the expandable member 42 with opposing lateral portions 24, 26 shown in a non-expanded, insertion configuration, and a pair of lateral support members 23 shown in a deformed, insertion configuration, is introduced between the adjacent superior and inferior spinous processes 16, 18. In this embodiment, the filling member 30 in the proximal lateral portion 24 of the expandable member 42 is coupled to a catheter 94, which will function as a conduit to deliver the flowable material. A syringe could be used in the alternative.

While the expandable member 42 is in a non-expanded, insertion configuration, the orientation and position of the medial portion 20, including rigid medial member 40, and the lateral portions 24, 26 of the expandable member 42 may be verified radiographically or endoscopically prior to introducing a measured amount of a flowable material via the catheter 94 to fill the expandable member 42 to the geometry. Exemplary flowable materials consist of polymers consisting of bone cement, polyurethane, silicon, copolymers of silicone and polyurethane, polyolefins, neoprene, nitrile or combinations thereof.

Figure 5D:
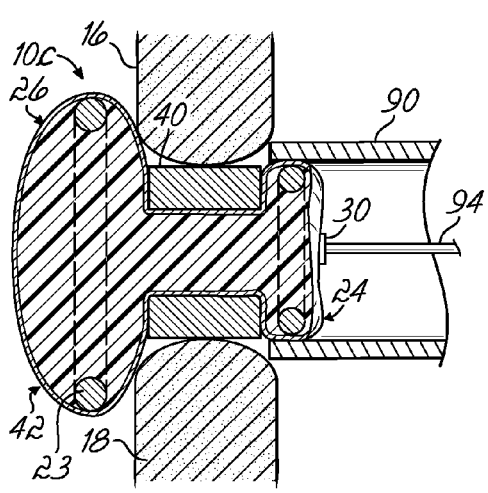
Figure 5E:
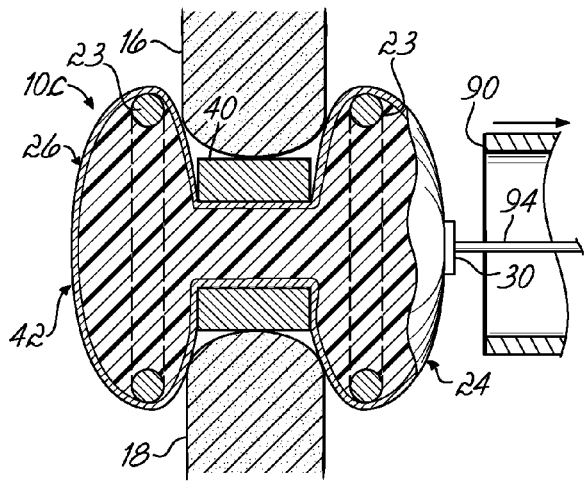
Figure 5A:
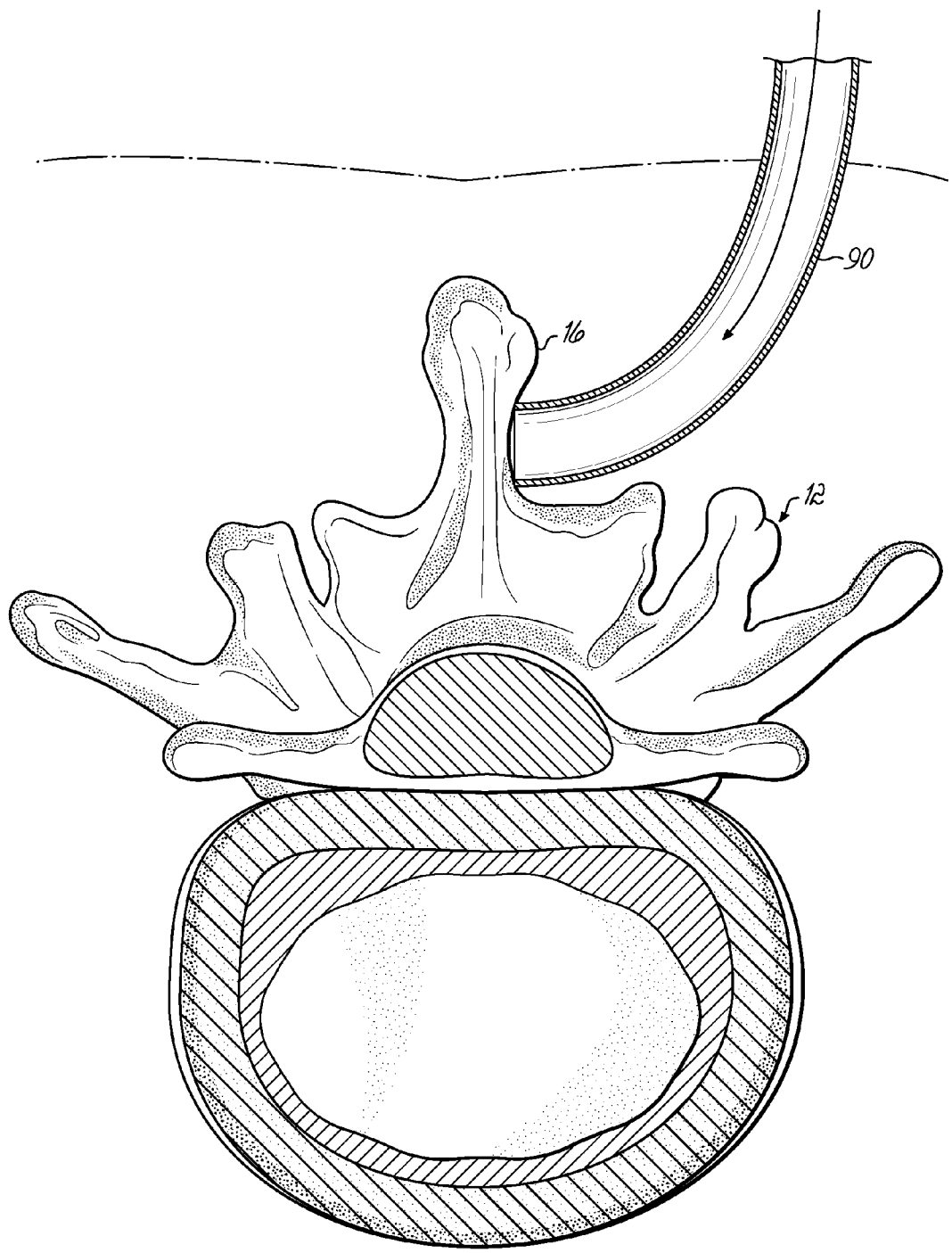

As depicted in FIG. 5D, the distal lateral portion 26 of expandable member 42 is first expanded by releasing the stress and/or force applied to the lateral support member 23 in distal lateral portion 26 to allow it to assume the deployed configuration and delivering a flowable material to the expandable member 42 through filling member 30 and through the rigid medial member 40. The presence of the delivery tube 90 surrounding the proximal lateral portion 24 hinders the expansion thereof. After the distal lateral portion 26 has achieved the desired level of expansion with support by its lateral support member 23, the delivery tube 90 is removed (or retracted) to allow the lateral support member 23 in proximal lateral portion 24 to assume the deployed configuration and the proximal lateral portion 24 to expand by continued feed of flowable material via catheter 94 through filling member 30, as depicted in FIG. 5E. After allowing time for the delivered flowable material to cure, the catheter body 94 is removed or severed from the filling member 30 of expandable member 42 containing the cured material. A connecting member may be used for fixation of the interspinous process spacer 10b in the desired space, as previously described. In this embodiment, and as described above, the flowable material may be heated or cooled to a temperature that causes the lateral support members to return to the deployed configuration. In other words, a shape memory material may be programmed (treated) to release the stress and thus release the elastic deformation in the presence of a designated temperature (or temperature range), either an elevated or a reduced temperature relative to the body temperature and/or the ambient (room) temperature, and that designated temperature condition may be provided by means of the flowable material. Alternatively, or in addition, the designated temperature may correspond to the expected body temperature in the desired space, such that the lateral support members self-expand upon retraction of the delivery tube and upon reaching the body temperature, which may be with or without assistance by heating the flowable material. In yet another alternative, the lateral support members 23 may be in the nature of a spring material, with the delivery tube 90 providing an applied compressive force, upon retraction of which the lateral support members 23 one by one spring back to the deployed configuration, thus self-expanding.

In an alternative embodiment of the invention, the method differs from that previously described in FIG. 5C by first introducing the rigid medial member 40 of FIG. 3, between the adjacent superior and inferior spinous process 16, 18 (method not illustrated). The expandable member 42 having expandable medial member 38 is introduced into the inter-process space, while in a deflated, insertion configuration, through the central, open space of the rigid medial member 40. In this embodiment, the expandable member 42 may have a geometry generally in the form of a dumbbell or an H-shape whereby the expandable medial member 38 may be positioned in the interprocess space within the hollow portion of the rigid medial member 40. The method according to this embodiment may be completed as previously described in FIGS. 5D and 5E.

Figure 4A:
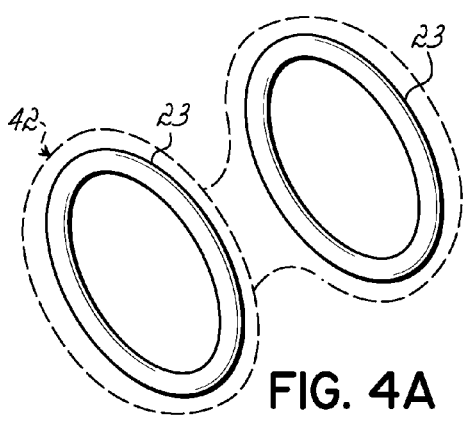
FIGS. 4A and 4B are perspective views depicting the lateral support members as rings and partial rings, respectively, in the lateral portions of the expandable member.
Figure 4B:
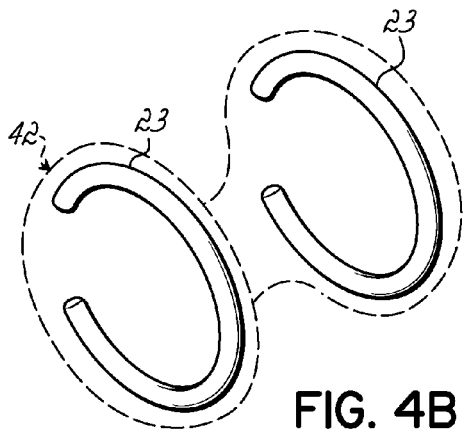
Figure 4C:
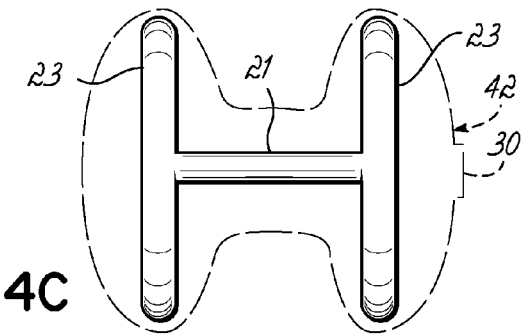
FIG. 4C is a rear elevational view depicting the lateral support members positioned in the lateral portions of the expandable member connected across the medial portion of the expandable member.

In yet another alternative embodiment, wherein lateral support members 23 are positioned in each of the opposing lateral portions 24, 26 of the interspinous process spacer 10d, as illustrated in FIG. 4A, an alternative method of implanting comprises elastically altering the shape of the lateral support members 23 to facilitate delivery through a delivery tube device to the space between the superior and inferior spinous processes 16, 18 of two adjacent vertebrae 12, 14. After the interspinous process spacer is positioned in the desired space between the superior and inferior spinous processes 16, 18 with the medial portion 20 therebetween, distal lateral portion 26 and a lateral support member 23 on a distal side of the space, and proximal lateral portion 24 and a lateral support member 23 on a proximal side of the space, the delivery tube device is retracted and the lateral support members 23 are allowed or caused to relax to their pre-altered shape, which will cause at least partial expansion of lateral portions 24, 26. In this embodiment, a shape memory material of the lateral support members 23 may be programmed to resume the deployed configuration at a temperature substantially equivalent to the temperature of the human body. Alternatively, a heated or cooled fluid may flushed into and subsequently removed from the lateral portions 24, 26 to provide the necessary thermal conditions for a programmed shape memory material. In yet another alternative, a spring-type material may be used that springs back to a non-deformed state upon retraction of the delivery tube device. The expandable member 42 can then be filled with flowable material, such as via a syringe or via a filling member and catheter, as previously described.

Figure 6:
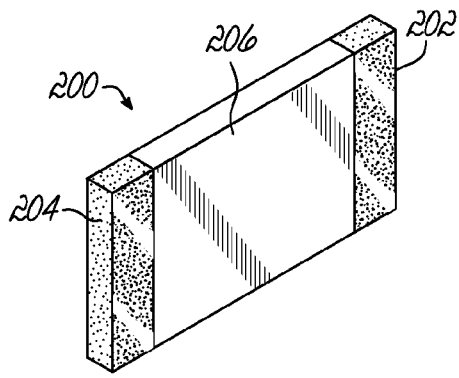
FIG. 6 is a perspective view of an interspinous process spacer in an alternative embodiment consistent with the present invention.
Figure 7:
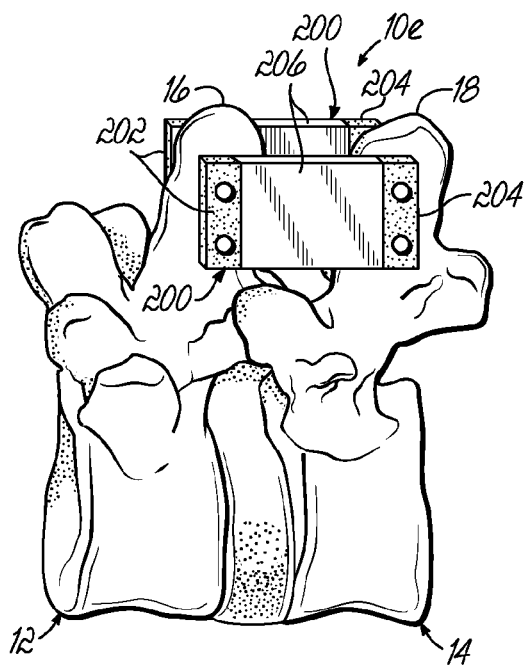
FIG. 7 is a perspective view depicting the spacer of FIG. 6 fastened to the lateral sides of the superior and inferior spinous processes.

In yet another embodiment within the scope of the invention is an interspinous process spacer 10e comprising at least one superior component 202, at least one inferior component 204 and at least one central component 206, as illustrated in FIGS. 6 and 7. The superior component 202 is adapted to reside on a lateral side of the superior spinous process 16 and to be affixed to the superior spinous process 16 when the spacer 10e is in the deployed configuration (i.e., when implanted into the body). The inferior component 204 is adapted to reside on a lateral side of the inferior spinous process 18 and to be affixed to the inferior spinous process 18 in the deployed configuration. In other words, the superior and inferior components 202, 204 are lateral portions intended and suited to be located laterally adjacent the spinous processes upon implantation. Additionally, the central component 206, which is adapted to reside on a lateral side of the interprocess space 34, connects the superior and inferior components 202, 204 to form a single member 200.

The superior and inferior components 202, 204 may comprise biocompatible metal or polymers, wherein at least the surface of the components consists of a porous material, such as Sulmesh®, which is a titanium-containing metal mesh. Other exemplary porous materials may comprise Trabecular Metal™, a fiber metal, a hydroxyapatite-coated material or any other suitable porous coated substrate such as Ti-VPS (vacuum plasma sprayed titanium coating) or Ti-APS (atmospheric plasma sprayed titanium coating), porous engineering polymer structures or combinations thereof, which may facilitate bone in-growth.

Moreover, the central component 206 may comprise a biocompatible elastomer, such as polycarbonate urethane. Other suitable materials may include poly(lactic acid), poly(glycolic acid), p-dioxanone fibers, polyarylethyl, polymethylmethacrylate, polyurethane, amino acid-derived polycarbonate, polycaprolactone, aliphatic polyesters, calcium phosphate, unsaturated linear polyesters, vinyl pyrrolidone, polypropylene fumarate diacrylate, or mixtures thereof. Of course, other suitable biocompatible materials are possible as well without departing from the scope of the present invention.

Figure 8:
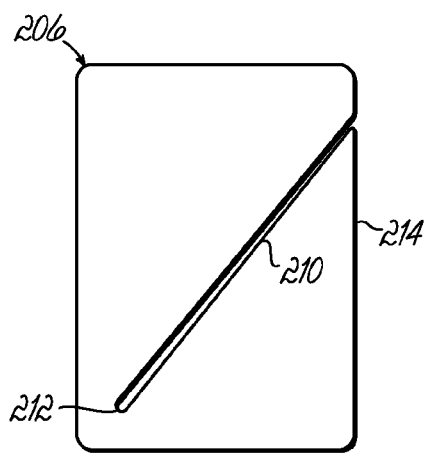
FIGS. 8 and 9 are elevated side views of an isolated central component of FIG. 6 providing a depiction of extension and flexions of a slot placed in the central component.
Figure 9:
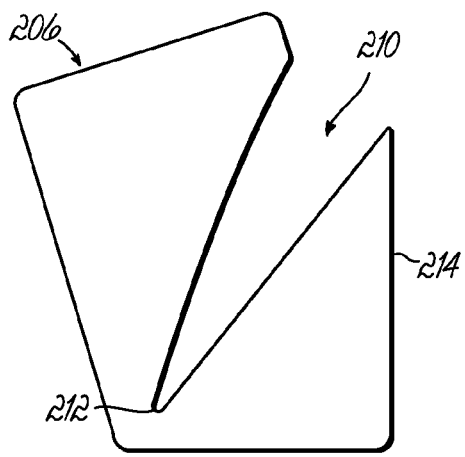
Figure 10:
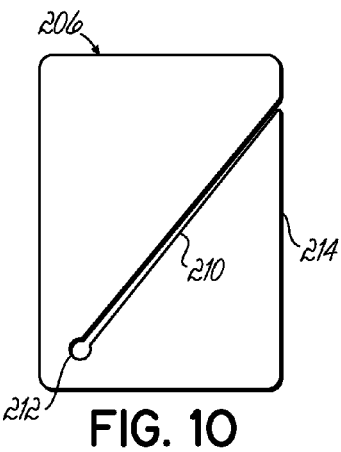
FIG. 10 through FIG. 24 are elevated side views of an isolated central component of FIG. 6 depicting exemplary embodiments of slots placed in the central component of the interspinous process spacer.
Figure 11:
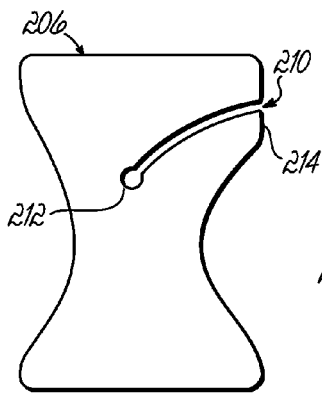
Figure 12:
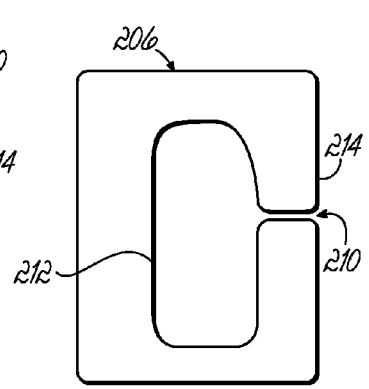
Figure 13:
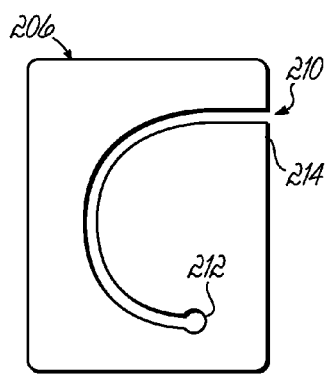
Figure 14:
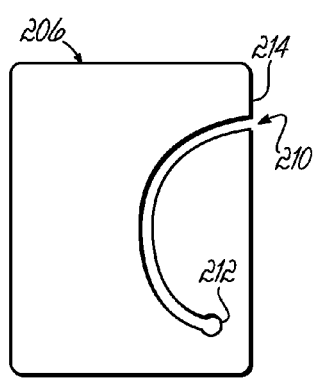
Figure 15:
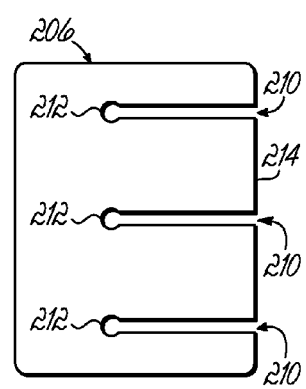
Figure 16:
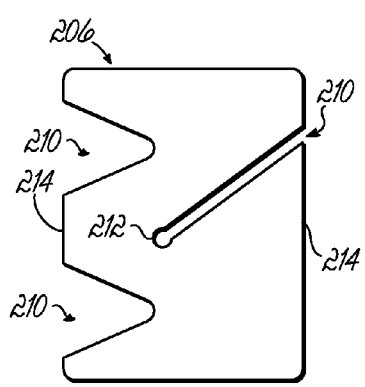

The central component 206 may be direct melted or injection molded to the superior and inferior components 202, 204 to form single member 200. The interspinous process spacer 10e of this embodiment may possess rigid characteristics in flexion and extension. As illustrated in FIGS. 8 and 9, a slot 210 may be introduced into the central component 206 to facilitate flexion (FIG. 9) and extension (FIG. 8), thereby reducing the overall rigidity. In this context, the term "slot" refers generally to a vacancy created in the central component 206 and does not denote any limitations to size or shape. As will be described and shown further below, more than one slot 210 may also be provided. Another aspect of the invention is enlarging a terminal end 212 (for example, see FIG. 14) of the aforementioned slot 210 to form a circular vacancy thereby reducing the flexion stress at this terminus.

Figure 17:
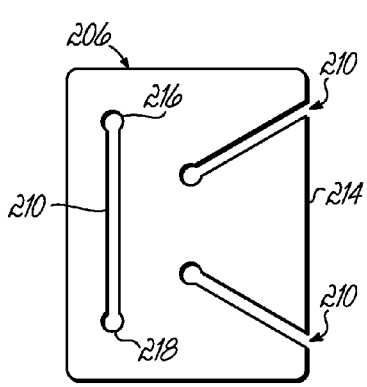
Figure 18:
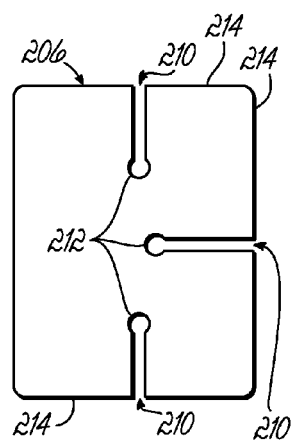
Figure 19:
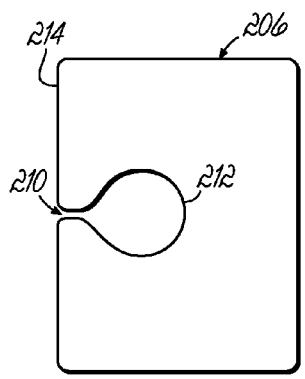
Figure 20:
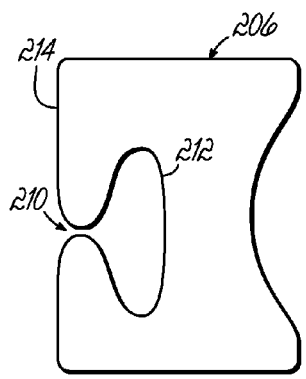
Figure 21:
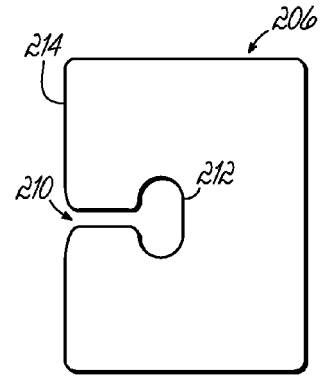
Figure 22:
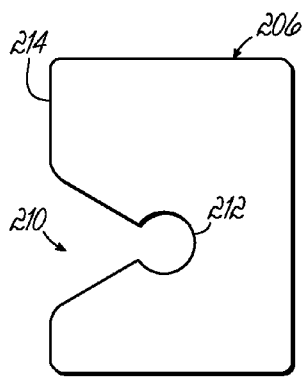
Figure 23:
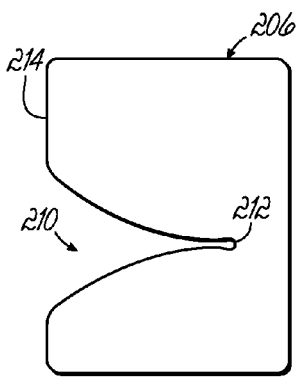
Figure 24:
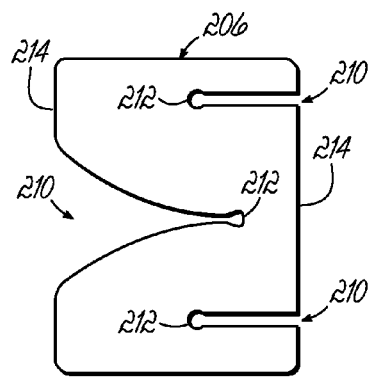
Figure 25:
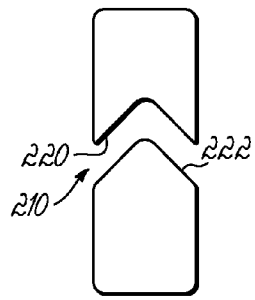
FIG. 25 through FIG. 27 are elevated edge views of an isolated central component of any of FIGS. 18 through 24 depicting exemplary embodiments of the internal surface of the slots to minimize torsional freedom or side-slippage of the two surfaces.
Figure 26:
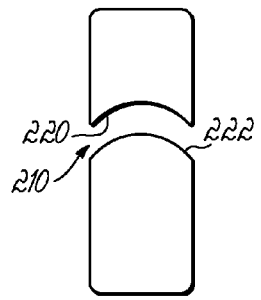
Figure 27:
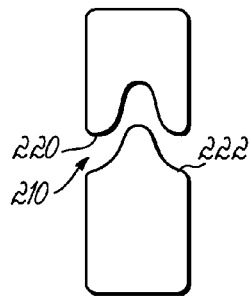

Referring to FIGS. 10 through 24, another aspect of the invention is varying the degree of flexibility or stiffness in flexion and extension by varying the location, size, shape, number and orientation of the slots 210. In some embodiments, the slots 210 begin from an edge 214 of the central component 206, proceed generally in a horizontal, vertical, diagonal, or curved direction, and terminate at an interior terminal end 212. In other embodiments, additional or alternative slots 210 may be internal, extending between terminal ends 216 and 218, and not extending to an exterior edge 214, such as shown in FIG. 17. In yet other embodiments, larger amounts of material may be removed to form a slot 210 to accommodate a customized flexibility (see, e.g., FIGS. 22-24). Moreover, the internal surfaces 220, 222 of the slots 210 may be shaped, as illustrated in FIGS. 25 through 27, to minimize torsional freedom or side-slippage of the two surfaces 220, 222.

Figure 28:
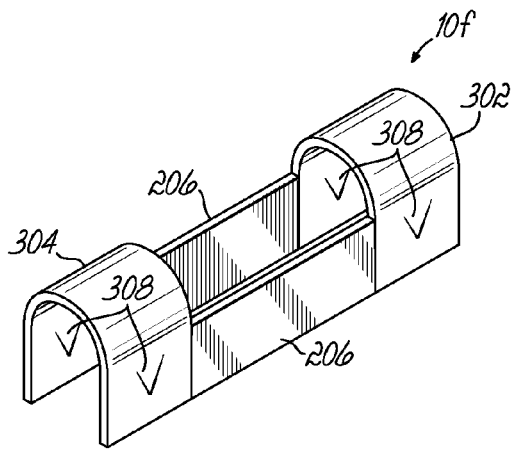
FIGS. 28-30 are perspective views of interspinous process spacers according to alternative embodiments consistent with the present invention.
Figure 29:
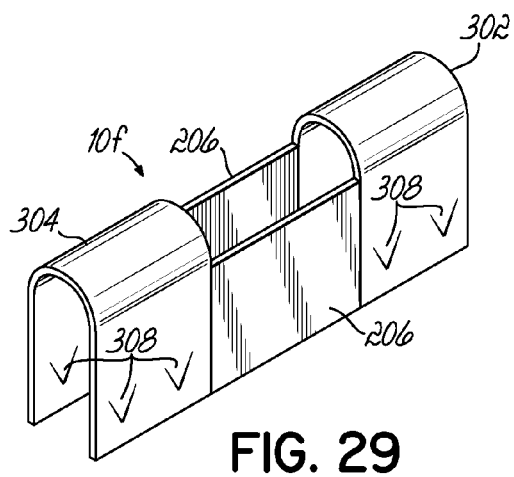
Figure 30:
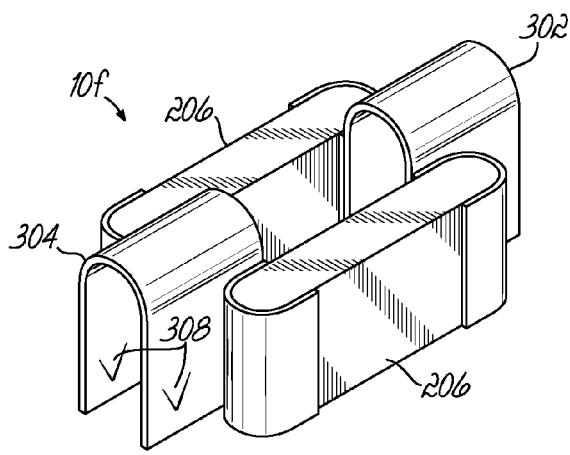

In an alternative embodiment of an interspinous process spacer 10f, a pair of central components 206 are connected between a superior component 302 and an inferior component 304, each configured in the form of a clip, as illustrated in FIG. 28. The clips 302, 304 may be made from biocompatible sheet metal, each having one or more notched teeth 308 for stability, as shown respectively in FIGS. 28 and 29. Moreover, the clips 302, 304 may have a titanium vacuum plasma sprayed coating thereon or the surfaces of the clips 302, 304 may consist of a porous material, such as Sulmesh® which is a titanium-containing metal mesh. Other exemplary porous materials include Trabecular Metal™, fiber metal, a hydroxyapatite-coated material, porous engineering polymer structures, or combinations thereof, which may facilitate bone in-growth. The pair of central components 206 may be direct melted, as illustrated in FIG. 30, or injection molded to the lateral portion of clips 302, 304 to form interspinous process spacer 10f, thereby providing bilateral support. The pair of central components 206 may contain one or more slots 210, as described above.

Figure 31:
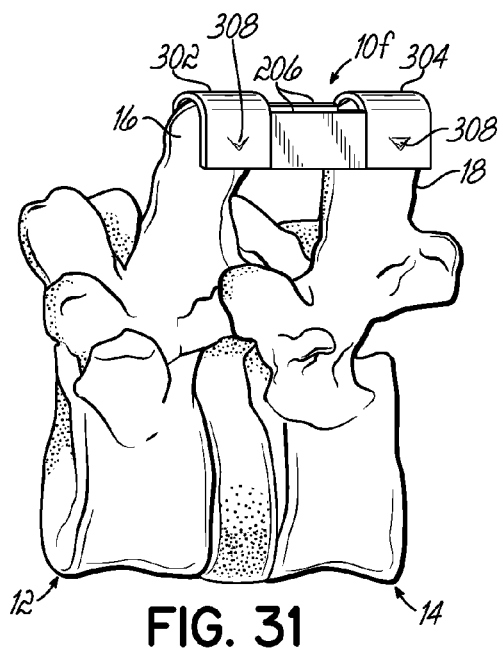
FIG. 31 is a perspective view depicting the spacer of FIG. 28 clamped to the lateral sides of the superior and inferior spinous processes.

In one intended use, the interspinous process spacer 10f, as illustrated in FIG. 31, may be attached to the superior and inferior spinous processes 16, 18 by being placed over the spinous processes and crimping the clips 302, 304 with forceps. The notched teeth 308 grip the bone for stability. In an alternative aspect, the superior and inferior clips 302, 304 of interspinous process spacer 10f and the superior and inferior components 202, 204 of interspinous process spacer 10e are adapted to be, and in use may be, affixed to their respective spinous processes 16, 18 by mechanical means, such as bone screws or bone darts.

Figure 32:
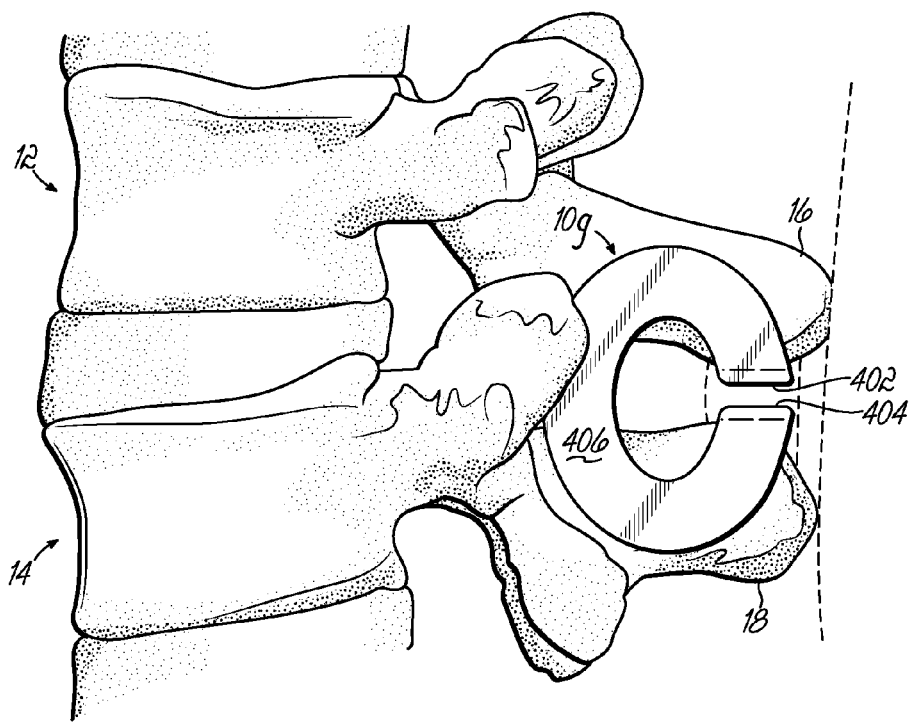
FIG. 32 is an elevated side view of an interspinous process spacer in an alternative embodiment consistent with the present invention, depicting end supports and a central connecting member positioned laterally to the superior and inferior spinous processes.
Figure 49:
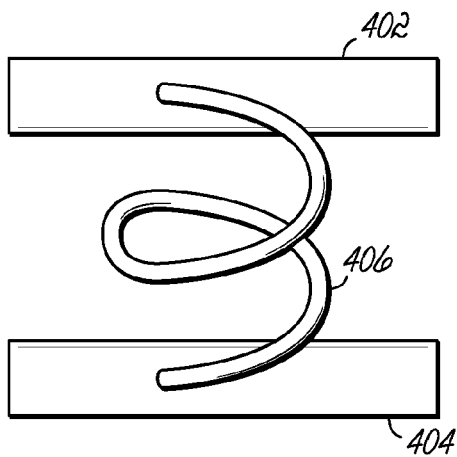
FIG. 49 and FIG. 50 show in side elevational view additional detail of the central connecting member of the interspinous process spacer of FIG. 32.
Figure 50:
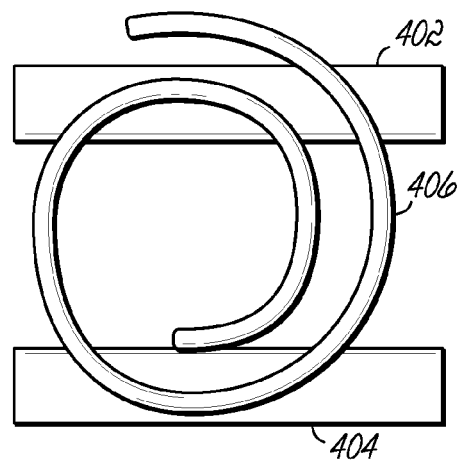

Another embodiment of an interspinous process spacer 10g of the invention is illustrated in FIG. 32. Interspinous process spacer 10g is a side-loaded elastic device, such as a spring, comprising first and second end supports 402, 404 and a central connecting member 406, wherein the central connecting member 406 is characterized by being adapted to reside laterally of the two spinous processes 16, 18 and being constructed from biocompatible spring steel. The central connecting member 406 may be constructed generally in the form of a C-shape. Alternative embodiments for central connecting member 406 may be constructed in different shapes, such as a spring or spiral, as exemplified in FIGS. 49 and 50, respectively.

Figure 33:
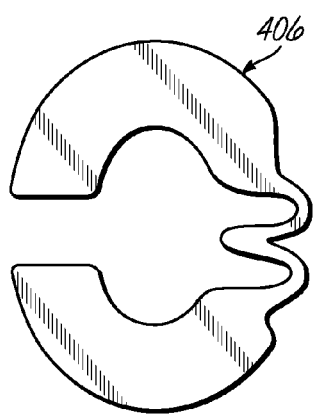
FIG. 33 through FIG. 35 illustrate in side elevational view alternative embodiments of the central connecting member of the interspinous process spacer of FIG. 32.
Figure 34:
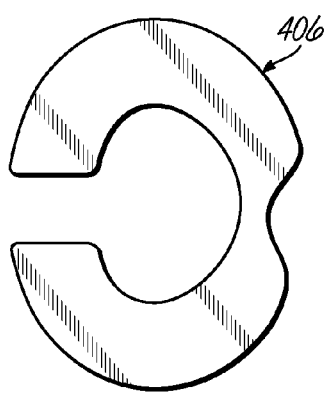
Figure 35:
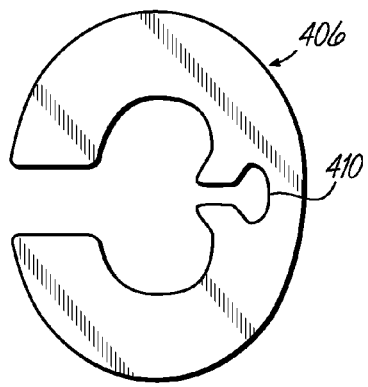

The interspinous process spacer 10g according to this embodiment may be undesirably too rigid. In this case, the relative stiffness or rigidity may be optimized by varying the cross-sectional area of the central connecting member 406, as illustrated in FIG. 33 through FIG. 35. Moreover, the central connecting member may be structured to provide a stop 410 in extension, as illustrated in FIG. 35.

Figure 36:
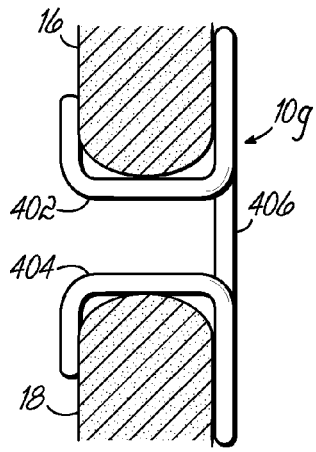
FIG. 36 through FIG. 38 illustrate in side elevational view alternative embodiments of shaped end supports of FIG. 32.
Figure 37:
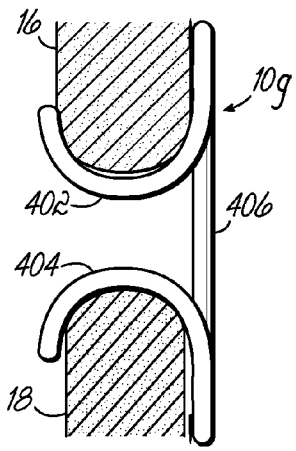
Figure 38:
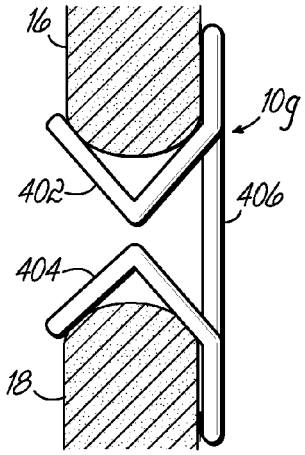
Figure 39:
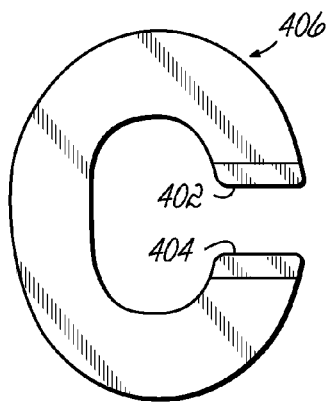
FIG. 39 through FIG. 41 illustrate in rear elevational view alternative embodiments of the end supports of FIG. 32.
Figure 40:
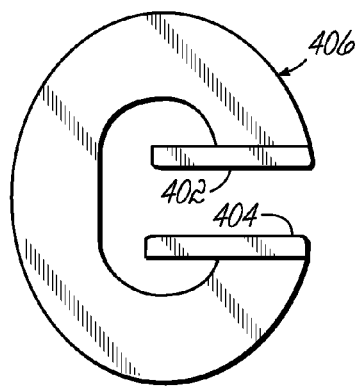
Figure 41:
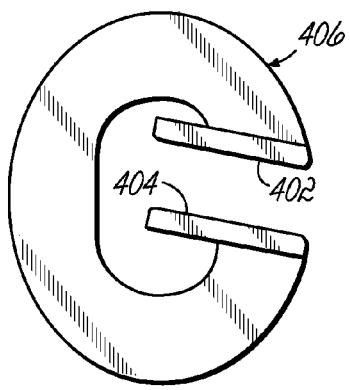

Another aspect to this embodiment is the first and second end supports 402, 404 possessing shaped configurations for accommodating the surfaces of the spinous processes 16, 18. The shaped end supports 402, 404 may be selected from a group consisting of generally flat, generally U-shaped, and generally V-shaped, as illustrated in FIG. 36, FIG. 37, and FIG. 38, respectively. Moreover, end supports 402, 404 may vary by providing short to wide support, as shown in FIG. 39 and FIG. 40, respectively, and may accommodate angular or tilted support, as shown in FIG. 41.

The shaped end supports 402, 404 may each further comprise a pre-formed liner 412, wherein each liner 412 conforms to the respective shaped end supports 402, 404, as illustrated in various embodiments in FIGS. 42 to 44, to accommodate spinous process seating. The liners 412 may also comprise one or more tabs 414 to enable fastening the liners 412 to their respective first and second end supports 402, 404. These liners 412 may be prepared from biocompatible polymers, such as polycarbonate urethane. Other suitable materials may comprise poly(lactic acid), poly(glycolic acid), p-dioxanone fibers, polyarylethyl, polymethylmethacrylate, polyurethane, amino acid-derived polycarbonate, polycaprolactone, aliphatic polyesters, calcium phosphate, unsaturated linear polyesters, vinyl pyrrolidone, polypropylene fumarate diacrylate, or mixtures thereof.

The interspinous process spacer 10g may comprise at least one fixation member, and advantageously at least one for each end support 402, 404, wherein the fixation members are selected from a group consisting of engaging teeth 420, bone darts 422, bone screws 424, and tying members 426, respectively illustrated in FIG. 45 through 48. Moreover, the spinous process 16 and/or 18 may be sculptured to accommodate fixation means.

Another aspect to this invention is a method of implanting an interspinous process spacer 10g according to this embodiment. The method comprises accessing the spinous processes 16, 18 from the lateral side and removing a section of the interspinous ligament to accommodate the first and second end supports 402, 404. The interspinous process spacer 10g is compressed using a compressing mechanism (not shown) and then the first and second end supports 402, 404 of the interspinous process spacer 10g are inserted between the superior and inferior spinous processes 16, 18, while the interspinous process spacer 10g is still in a compressed configuration. The position may be verified. The compression mechanism is released and the interspinous process spacer 10g is allowed to spring open to distract the spinous processes 16, 18 of the adjacent vertebrae 12, 14.

While the present invention has been illustrated by a description of various embodiments and while these embodiments have been described in considerable detail, it is not the intention of the applicants to restrict or in any way limit the scope of the appended claims to such detail. The described embodiments are simply intended to clarify the technical idea of the present invention. As such, the technical scope of the present invention should not be construed solely on the basis of the specific embodiments described above. Additional advantages and modifications will readily appear to those skilled in the art. The invention in its broader aspects is therefore not limited to the specific details, representative aspects and methods, and illustrative examples shown and described. Accordingly, departures may be made from such details without departing from the scope of applicant's general inventive concept.

What is claimed is:

1. An interspinous process spacer for maintaining separation between adjacent superior and inferior spinous processes of two adjacent vertebrae when in a deployed configuration, the interspinous process spacer comprising:
   a first lateral portion, a second lateral portion, and a medial portion therebetween;
   wherein the medial portion is adapted to reside between the adjacent superior and inferior spinous processes in the deployed configuration to maintain separation therebetween;
   wherein the first and second lateral portions each comprise a superior lateral portion adapted to reside on the lateral side of the superior spinous process in the deployed configuration and an inferior lateral portion adapted to reside on the lateral side of the inferior spinous process in the deployed configuration to maintain positioning of the interspinous process spacer between the two adjacent vertebrae;
   wherein the first and second lateral portions each comprise an expandable lateral member that is expandable from an insertion configuration to the deployed configuration; and
   wherein at least one of the first and second lateral portions comprises a separate lateral support member disposed inside an interior of the expandable lateral member, the lateral support member configured to be deformable for the insertion configuration and expanded in the deployed configuration.

2. The interspinous process spacer of claim 1, further comprising:
   a flowable material for expanding the expandable lateral members in-situ.

3. The interspinous process spacer of claim 2 wherein the flowable material is a polymer consisting of bone cement, polyurethane, silicone, copolymers of silicone and polyurethane, polyolefins, neoprene, nitrile or combinations thereof.

4. The interspinous process spacer of claim 1, further comprising:
   at least one connecting member used for fixation of the interspinous process spacer in a desired position between the two adjacent vertebrae.

5. The interspinous process spacer of claim 1 wherein the expandable lateral members are made of compliant material fabricated to a geometry that will maintain the geometry when expanded to a desired position on the lateral sides of the spinous processes.

6. The interspinous process spacer of claim 1 wherein the expandable lateral members are made of non-compliant material fabricated to a geometry that will be assumed when expanded to a desired position on the lateral sides of the spinous processes.

7. The interspinous process spacer of claim 1 wherein the medial portion comprises an expandable medial member.

8. The interspinous process spacer of claim 7 wherein the medial portion further comprises a tubular rigid medial member positioned around the expandable medial member and adapted to reside between the adjacent superior and inferior spinous processes to maintain the separation therebetween.

9. The interspinous process spacer of claim 7 wherein the medial portion further comprises a rigid medial member positioned within the expandable medial member and adapted to reside between the adjacent superior and inferior spinous processes to maintain the separation therebetween.

10. The interspinous process spacer of claim 7 wherein the expandable lateral members and the expandable medial member form a single, seamless expandable member.

11. The interspinous process spacer of claim 10 wherein the single, seamless expandable member is fabricated so as to have a dumbbell-shaped geometry in the deployed configuration.

12. The interspinous process spacer of claim 1 wherein the medial portion comprises a rigid medial member connected to the expandable lateral members, the rigid medial member adapted to reside between the adjacent superior and inferior spinous processes to maintain the separation therebetween.

13. The interspinous process spacer of claim 1 wherein each of the first and second lateral portions comprises a lateral support member.

14. The interspinous process spacer of claim 1 wherein the lateral support member is made of a shape memory material configured to maintain a deformed state as the insertion configuration at approximately room temperature and to expand to re-assume a non-deformed state as the deployed configuration in the presence of a temperature different than the approximate room temperature.

15. The interspinous process spacer of claim 14, wherein the temperature different than the approximate room temperature is approximately that of a body temperature at the adjacent vertebrae.

16. The interspinous process spacer of claim 1 wherein the lateral support member is made of a spring material configured to be deformed to the insertion configuration by a compressive force and to expand to the deployed configuration upon removal of the compressive force.

17. An interspinous process spacer for maintaining separation between adjacent superior and inferior spinous processes of two adjacent vertebrae when in a deployed configuration, the interspinous process spacer comprising:
an expandable member comprising a first expandable lateral portion, a second expandable lateral portion, and an expandable medial portion therebetween, each configured to expand from an insertion configuration to an expanded, deployed configuration;
a tubular rigid medial member cooperating with the expandable medial portion, wherein the expandable medial portion and tubular rigid medial member are adapted to reside between the adjacent superior and inferior spinous processes in the expanded, deployed configuration to maintain separation therebetween; and
first and second separate lateral support members residing inside an interior of the respective first and second expandable lateral portions, the first and second lateral support members configured to be deformable for the insertion configuration and expanded in the deployed configuration, wherein the first and second expandable lateral portions and lateral support members each comprise a superior lateral portion adapted to reside on the lateral side of the superior spinous process in the expanded, deployed configuration and an inferior lateral portion adapted to reside on the lateral side of the inferior spinous process in the expanded, deployed configuration to maintain positioning of the interspinous process spacer between the two adjacent vertebrae.

18. The interspinous process spacer of claim 17 wherein the first and second lateral support members are made of a shape memory material configured to maintain a deformed state as the insertion configuration at approximately room temperature and to expand to re-assume a non-deformed state as the expanded, deployed configuration in the presence of a temperature different than the approximate room temperature.

19. A method for implanting an interspinous process spacer for maintaining separation between adjacent superior and inferior spinous processes of two adjacent vertebrae, the method comprising:
introducing a tubular delivery device to a region between the adjacent superior and inferior spinous processes;
introducing an interspinous process spacer having a non-expanded, insertion configuration and an expanded, deployed configuration through the tubular delivery device in the non-expanded, insertion configuration to the region, the interspinous process spacer comprising an expandable member having a distal lateral portion with a separate distal lateral support member disposed inside an interior of the distal lateral portion, a medial portion, and a proximal lateral portion with a separate proximal lateral support member disposed inside an interior of the proximal lateral portion, and positioning the distal lateral portion on a distal side of the spinous processes, the medial portion between the spinous processes, and the proximal lateral portion on a proximal side of the spinous processes; and
retracting the tubular delivery device and expanding the expandable member and the distal and proximal lateral support members to the expanded, deployed configuration.

20. The method of claim 19 wherein the distal and proximal lateral support members each self-expand to the deployed configuration upon removal of the tubular delivery device.

21. The method of claim 19 further comprising:
verifying the orientation and position of the tubular delivery device and the expandable member radiographically or endoscopically.

22. The method of claim 19 wherein expanding the expandable member includes introducing a measured amount of a flowable material to fill the expandable member to the expanded, deployed configuration; and further comprising:
curing the delivered flowable material.

23. The method of claim 19 wherein the flowable material is a polymer consisting of bone cement, polyurethane, silicon, copolymers of silicone and polyurethane, polyolefins, neoprene, nitrile or combinations thereof.

24. The method of claim 19 further comprising;
fixing the interspinous process spacer to at least one of the superior or inferior spinous processes or a neighboring tissue in the region with a connecting member.

* * * * *